US00PP17758P2

(12) United States Plant Patent
Bradford

(10) Patent No.: US PP17,758 P2
(45) Date of Patent: May 22, 2007

(54) PEACH TREE NAMED 'DIAMOND CANDY'

(50) Latin Name: *Prunus persica*
Varietal Denomination: Diamond Candy

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/311,240

(22) Filed: Dec. 20, 2005

(51) Int. Cl.
*A01H 5/00* (2006.01)

(52) U.S. Cl. ..... Plt./198
(58) Field of Classification Search ..... Plt./198
See application file for complete search history.

(56) References Cited

U.S. PATENT DOCUMENTS

| | | | | |
|---|---|---|---|---|
| PP8,948 P | | 10/1994 | Bradford | |
| PP13,392 P2 | * | 12/2002 | Slaughter et al. | Plt./198 |
| PP14,677 P2 | | 4/2004 | Bradford | |

* cited by examiner

*Primary Examiner*—Wendy Haas

(57) ABSTRACT

The present invention relates to a peach tree, *Prunus persica,* and more particularly to a new and distinct variety characterized by a medium size, vigorous, hardy, self-fertile, productive and regular bearing tree. The fruit matures under the ecological conditions described in the latter part of June, with first picking on Jun. 22, 2005. The fruit is uniformly large in size, sub-acid and sweet in flavor, globose in shape, freestone in type, firm in texture, yellow with only minor red streaking in flesh color, and mostly red in skin color.

1 Drawing Sheet

Botanical classification: *Prunus persica.*
Variety denomination: 'Diamond Candy'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of peach tree, which has been denominated varietally as 'Diamond Candy'. The present variety was hybridized by me in 1996, grown as a seedling on its own root in my greenhouse, and transplanted to a cultivated area of my experimental orchard near Le Grand, Calif., in Merced County (San Joaquin Valley).

The variety was developed as a first generation cross using 'Diamond Ray' (U.S. Plant Pat. No. 8,948) yellow flesh nectarine as the selected seed parent and an unnamed peach (unpatented) as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed parent, 'Diamond Ray' (U.S. Plant Pat. No. 8,948) nectarine, by producing fruit that is globose in shape, firm in texture, full red in skin color, yellow in flesh color, and that ripens in the latter part of June, but is very distinguished therefrom by producing fruit that is freestone instead of clingstone, that is sub-acid instead of acid in flavor, and that is peach instead of nectarine in type.

The present variety is similar to 'Spring Candy' (U.S. Plant Pat. No. 14,677) peach by producing freestone peaches that are yellow in flesh color, sub-acid in flavor, globose in shape, and firm in texture, but is distinguished therefrom by producing peaches that have much less red bleeding around the stone and that mature eight days later, extending the season for this type of fruit. It is to be noted that in 2005 fruit matured earlier in the season than most years, with 'Spring Candy' beginning harvest on Jun. 14, 2005.

SUMMARY OF VARIETY

In summary, the present variety is characterized by a medium size, vigorous, hardy, self-fertile, productive and regular bearing tree. The fruit matures under the ecological conditions described in the latter part of June, with first picking on Jun. 22, 2005. The fruit is uniformly large in size, sub-acid and sweet in flavor, globose in shape, freestone in type, firm in texture, yellow with only minor red streaking in flesh color, and mostly red in skin color.

DRAWING

The accompanying photograph exhibits four whole fruits positioned to display the characteristics of the skin color and form, one fruit divided around the suture plane to reveal the flesh and stone, two mature leaves, and a blossom in full bloom in the lower inset.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 24, 2005, on the original tree during its ninth growing season. All major color code designations are by reference to the Inter-Society Color Council, National Bureau of Standards. Common color names are also used occasionally.

Tree

Size: Medium, reaching a height of 11' [3.35 m.] and a spread of 10' [3.05 m.] after nine growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Approximate chilling requirement: 550 hours.

Trunk:

*Size.*—Medium with a maximum diameter of 4" [102 mm.] after the nine growing seasons.

*Texture.*—Very shaggy.

*Bark color.*—A two tone variegation of Grayish yellowish brown [80. gy.yBr] and Moderate brown [58. m.Br].

*Lenticels.*—Approximate Number Per Square Inch: 12. Color: Light yellowish brown [76. l.yBr]. Size: ⅛" to 7/16" [3.2–11.1 mm.]. Shape: Eye-shaped to elongated.

Branches:

*Size.*—Diameter of limb is 2½" [63.5 mm.] measured 12" from the crotch.

*Texture.*—Shaggy.

*Color.*—1st Year Wood Topside: Grayish red [19. gy.R]. 1st Year Wood Underside: Brilliant yellow green [116. brill.YG]. Older Wood: Dark yellowish brown [78. d.yBr].

*Lenticels.*—Approximate Number Per Square Inch: 30. Color: Moderate orange yellow [71. m.OY]. Size: 1/16" to 3/16" [1.6–4.8 mm.]. Shape: Eye-shaped to elongated.

Leaves:

*Size.*—Medium. Average Length: 5⅛" [130 mm.]. Average width: 1⅜" [35 mm.].

*Arrangement.*—Alternate.

*Thickness.*—Medium.

*Form.*—Elliptical.

*Apex.*—Acuminate.

*Base.*—Obtuse, with an average base angle of 100 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ½" [12.7 mm.]. Average Thickness: 1/16" [1.6 mm.]. Color: Light yellow green [119. l.YG].

*Stipules.*—Number: 2 per leaf, up to 6 per growing tip. Average Length: ⅜" [9.5 mm.]. Color: Brilliant yellow green [116. brill.YG] when young becoming Moderate reddish brown [43. m.rBr] with age.

*Glands.*—Number: 4 to 8, average of 6. Position: Slightly alternate in pairs, two positioned on petiole and the rest on base of leaf blade. Size: Small. Form: Reniform when older, but very young glands look somewhat globose. Color: Light yellow green [119. l.YG] when young with centers becoming Dark reddish brown [44. d.rBr] with age.

*Leaf buds.*—Pointed to conic, small.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Strong purplish pink [247. s.pPk].

Flowers: Perfect, complete, perigynous, usually a single pistil, typically thirty or more stamens, five sepals and petal locations alternately positioned.

*Type.*—Showy, large.

*Average flower diameter.*—1¾" [44.5 mm.].

*Number of petals.*—Usually five, with double blossoms rarely observed.

*Petal shape.*—Circular.

*Petal margin.*—Somewhat wavy.

*Average petal diameter.*—11/16" [17.5 mm.].

*Average petal length.*—¾" [19.1 mm.].

*Petal apex.*—Rounded.

*Petal base.*—Rounded.

*Petal color.*—Pale pink [7. p.Pk] toward the apex, Moderate purplish pink [250. m.pPk] toward the base.

*Anther color.*—Dark red [16. d.R] over Light orange yellow [70. l.OY] centers at bloom onset.

*Stigma color.*—Light greenish yellow [101. l.gY].

*Sepal color.*—Dark purplish red [259. d.pR].

*Sepal length.*—¼" [6 mm.].

*Sepal width.*—3/16" [5 mm.].

*Average pistil length.*—⅝" [15.9 mm.].

*Average stamen length.*—⅝" [15.9 mm.].

*Fragrance.*—Moderate.

*Blooming period.*—Early to medium compared with other varieties.

*Onset of bloom.*—One percent on Feb. 16, 2005.

*Date of full bloom.*—Feb. 24, 2005.

*Duration of bloom.*—One to two weeks, dependent on ambient temperature.

*Number per cluster.*—1 to 3 with single flowers most common.

FRUIT

Maturity when described: Firm ripe, Jun. 26, 2005.

Date of first picking: Jun. 22, 2005, noting that in 2005 fruit matured about two weeks earlier than normal.

Date of last picking: Jul. 3, 2005.

Size: Uniform, large.

*Average diameter axially.*—3" [76.2 mm.].

*Average diameter across suture plane.*—3⅛" [79.5 mm.].

*Typical weight.*—7.9 ounces [224 grams].

Form: Uniform, symmetrical, globose with some axial compression on most.

*Longitudinal section form.*—Circular to slightly elliptical.

*Axial view.*—Circular.

Suture: A sharp groove at the base becoming an inconspicuous line along the side, a shallow groove near the apex, and extending beyond the pistil point with minor depressions on both sides.

Ventral surface: Rounded, lipped toward the apex on one side.

Lips: Somewhat unequal.

Cavity: Flaring, elongated in the suture plane, suture showing on both sides, Brilliant yellow [83. brill.Y] stem markings typical.

*Depth.*—½" [12.7 mm.].

*Breadth.*—13/16" [20.6 mm.].

Base: Slightly truncate.

Apex: Rounded.

Pistil point: Usually oblique, usually short, 75 percent are depressed within the suture and 25 percent are somewhat mammiform.

Stem: Large.

*Average length.*—7/16" [11.1 mm.].

*Average width.*—3/16" [4.8 mm.].

Skin:

*Thickness.*—Medium.

*Texture.*—Pubescent.

*Tenacity.*—Tenacious to flesh.

*Astringency.*—Nonastringent.

*Tendency to crack.*—None observed.

*Color.*—Very dark red [17. v.d.R] over a Dark reddish orange [38. d.rO] background.

Down: Moderate, short in length, does not roll up when rubbed.

Flesh:

*Color.*—Brilliant Yellow [83. brill.Y] from skin to near stone with very minimal Strong red [12. s.R] streaking very close to the stone.

*Surface of pit cavity.*—Covered with Strong red [12. s.R] fibers.

*Amygdalin.*—Scarce.

*Juice.*—Moderate, rich.

*Texture.*—Very Firm and crisp.

*Fibers.*—Abundant, fine.

*Ripens.*—Slightly earlier at the apex along the lips.

*Flavor.*—Sub-acid, mild and sweet, typically 15 brix.

*Aroma.*—Very slight.

*Eating quality.*—Very good.

STONE

Type: Freestone.

Form: Oval.

Hilum: Narrow.

Base: Straight.

Apex: Acute, with an average base angle of 90 degrees and a tip length of ⅛" [3.2 mm.].

Sides: Equal.

Surface: Irregularly furrowed toward the apex and pitted toward the base.

Ridges: Jagged toward the base.

External color: Moderate brown [58. m.Br] with Deep red [13. deep R] staining from the fruit fibers.

Internal color: Light brown [57. l.Br].

Average pit wall thickness: ¼" [6.4 mm.].

Average width: 1⅛" [28.7 mm.].

Average length: 1½" [38.1 mm.].

Average breadth: 13/16" [20.6 mm.].

Tendency to split: None observed.

Kernel:

*Form.*—Oval.

*Pellicle color.*—Grayish yellowish brown [80. gy.yBr].

*Skin color.*—Light yellow [86. l.Y].

*Vein color.*—Light grayish yellowish brown [79. l.gy.yBr].

*Taste.*—Bitter.

*Viable.*—Yes.

*Average width.*—15/32" [11.9 mm.].

*Average length.*—13/16" [20.6 mm.].

*Amygdalin.*—Abundant.

USE

Market: Fresh market and long distance shipping.

Keeping quality: Good. Fruit quality observed to remain in good condition in after 21 days in standard cold room at 36° Fahrenheit [2° Celsius].

Shipping quality: Good.

Resistance to insects: No unusual susceptibilities noted.

Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is similar to 'Spring Candy' (U.S. Plant Pat. No. 14,677) peach by producing freestone peaches that are yellow in flesh color, sub-acid in flavor, globose in shape, and firm in texture, but is distinguished therefrom by producing peaches that have much less red bleeding around the stone and that mature eight days later, extending the availability of this type of fruit.

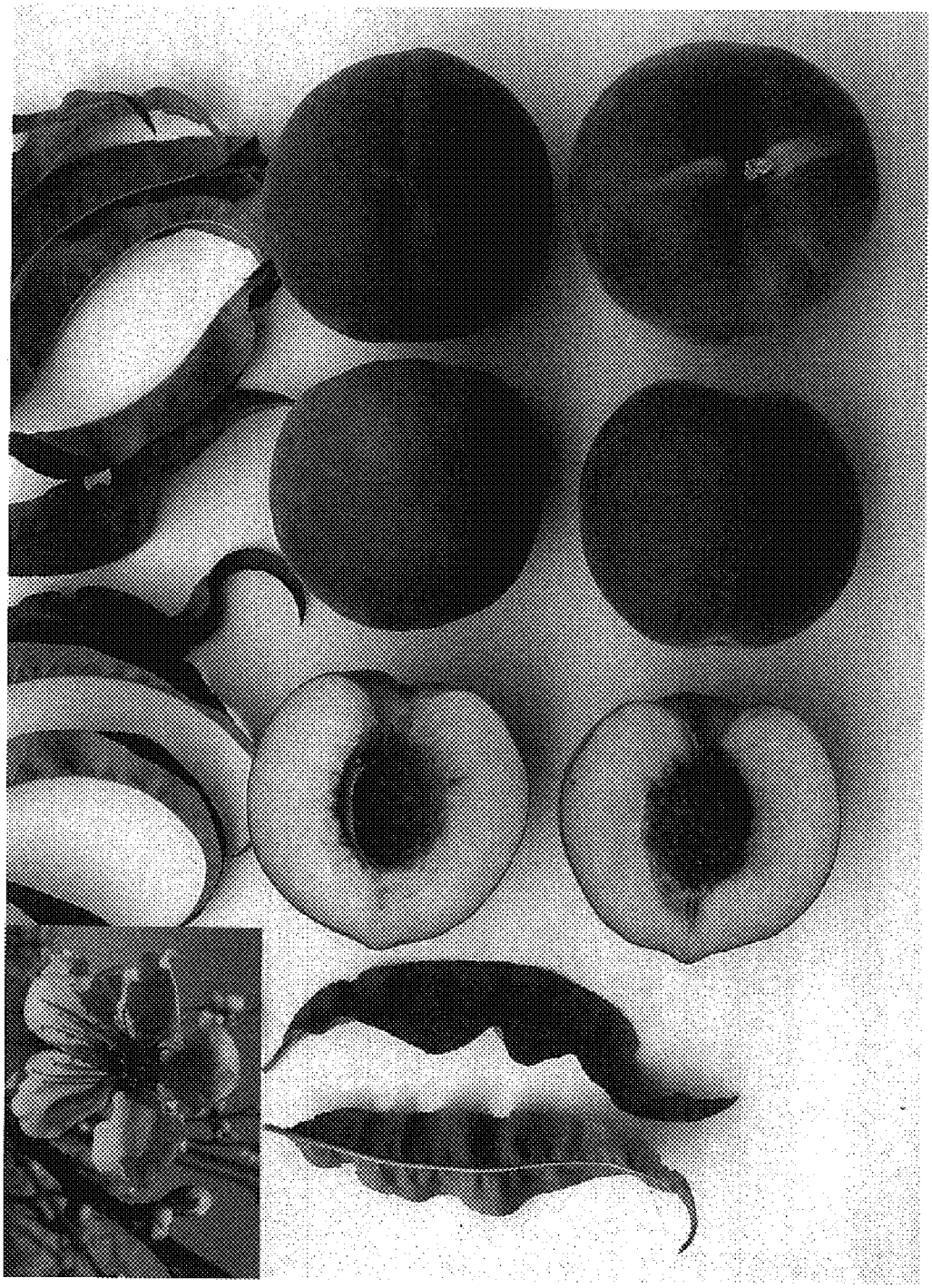

* * * * *